United States Patent [19]

Empey et al.

[11] 4,263,399

[45] Apr. 21, 1981

[54] HIGH PHOSPHATE PROCESS FOR MAKING LOW CALCIUM, SMOOTH FLOW XANTHAN GUM

[75] Inventors: Richard A. Empey, Tulsa, Okla.; Jurgen G. Dominik, Bonita, Calif.

[73] Assignee: Merck & Co., Inc., Rahway, N.J.

[21] Appl. No.: 44,144

[22] Filed: May 31, 1979

[51] Int. Cl.$^3$ .............................................. C12P 19/06
[52] U.S. Cl. .................................... 435/104; 435/244; 435/910
[58] Field of Search ......................................... 435/104

[56] References Cited

U.S. PATENT DOCUMENTS

| | | | |
|---|---|---|---|
| 3,000,790 | 9/1961 | Jeanes et al. | 435/104 |
| 3,433,708 | 3/1969 | McNeely | 435/104 |
| 3,594,280 | 7/1971 | Cohn et al. | 435/104 |
| 3,933,788 | 1/1976 | Kang et al. | 435/104 X |
| 4,119,546 | 10/1978 | Wernau | 252/8.55 D |
| 4,135,979 | 1/1979 | Corley et al. | 435/104 X |
| 4,154,654 | 5/1979 | Campagne | 435/104 |

*Primary Examiner*—Lionel M. Shapiro
*Attorney, Agent, or Firm*—Gabriel Lopez; Hesna J. Pfeiffer; Julian S. Levitt

[57] ABSTRACT

A novel process is described for making a low calcium xanthan gum exhibiting smooth flow properties which comprises the use of high levels of phosphate in the fermentation medium.

5 Claims, No Drawings

HIGH PHOSPHATE PROCESS FOR MAKING LOW CALCIUM, SMOOTH FLOW XANTHAN GUM

CROSS REFERENCE

This invention is related to U.S. Ser. No. 44,145, filed on May 31, 1979, entitled "Low Calcium Xanthan Gums".

BACKGROUND OF THE INVENTION

The preparation and uses of xanthan gum are well known to those skilled in the field of heteropolysaccharides. While aqueous compositions of xanthan gum have many desirable properties, such compositions have a chunky or non-uniform flow.

OBJECTS OF THE INVENTION

It is an object of the present invention to provide a means of making low calcium smooth flow xantham gum without the necessity of imparting high shear to the media during fermentation.

SUMMARY OF THE INVENTION

Xanthan gum having not more than about 400 ppm of calcium is prepared from an aqueous fermentation medium substantially free of calcium ion and substantially free of fermentation nutrients which contain calcium. When prepared under conditions of high shear the gum provides aqueous oil/water compositions having smooth or uniform flow.

DETAILED DESCRIPTION

Aqueous compositions of xanthan gum tend to have a "chunky" or non-uniform flow characteristic. A "chunky" flow is an uneven, lumpy type of flow such as is encountered with tomato catsup. A smooth or uniform type of flow is one free of lumps and unevenness such as is encountered with vegetable oil.

It has now been found that there is a correlation between the calcium content of xanthan gum and the flow characteristics of aqueous compositions containing xanthan gum. The aqueous compositions include solutions of xanthan gum as well as oil/water emulsions. In general, aqueous compositions of xanthan gum containing not more than about 0.04 weight % of calcium and fermented under high shear conditions have desirable flow properties, and aqueous compositions of xanthan gum containing not more than about 0.02 weight % of calcium and fermented under high shear conditions have best flow properties.

The low calcium xanthan gum of the present invention may be prepared by a heteropolysaccharide-producing bacterium, *Xanthomonas campestris* by the whole culture fermentation of a medium comprising a fermentable carbohydrate, a nitrogen source, and appropriate other nutrients.

The bacterium is grown in a medium which is substantially free of calcium ions. By substantially free is meant up to about 4 ppm of calcium ion per each 1% of xanthan gum concentration in the completed fermentation broth, and preferably up to about 2 ppm of calcium per each 1% of xanthan gum concentration in the completed fermentation broth. Thus, if the xanthan gum is to be produced at a final concentration of about 2.1–2.3%, the total calcium ion content of the completed fermentation broth should not exceed about 9 ppm and preferably should not exceed about 5 ppm. To obtain such a low calcium medium the calcium content of the water in the fermentation medium may be reduced to the appropriate level by any means such as by chemical means, e.g., ion-exchange treatment, or by distillation, or by the use of soft water. As commercial sources of organic nitrogen contain appreciable amounts of calcium ion, it is important that the nitrogen source of the present invention be a material which is substantially free of calcium ions. An example of such a nutrient material is Promosoy 100, a soy protein concentrate (Central Soya). Use of this material at 500 ppm imparts 1–2 ppm calcium to the medium.

The relationship between the total calcium ion content of the fermentation media, the final xanthan gum concentration in the broth, and the calcium ion content of the isolated xanthan gum is expressed in Table 1.

TABLE 1

| Calcium Ion Relationships | | |
|---|---|---|
| Total Calcium Ion of Media (ppm) | Final Xanthan Gum Concentration (%) | Calcium Content of Xanthan Gum (ppm) |
| 12 | 3 | 400 |
| 8 | 2 | 400 |
| 4 | 1 | 400 |
| 6 | 3 | 200 |
| 4 | 2 | 200 |
| 2 | 1 | 200 |

Prior art fermentations of xanthan gum failed to appreciate the benefits obtainable by low concentrations of calcium and, indeed, teach the addition of calcium either to the fermentation beer or to the reconstituted xanthan gum. Examples of such prior art teachings are U.S. Pat. Nos. 3,000,790, 3,054,689, 3,096,293, 3,232,929 and 4,053,699 and French Pat. No. 2,330,697.

In addition the prior art teaches the use of tap water rather than deionized water, not only because of economic considerations, but because tap water contains trace elements required for growth of the gum-producing organism. See, for example, "Polysaccharide (Xanthan) of *Xanthomonas campestris* NRRL B-1459: Procedures for Culture Maintenance and Polysaccharide Production, Purification and Analysis", Agricultural Research Service, U.S. Department of Agriculture (ARS-NC-51).

Moreover, the prior art teaches the use of distillers solubles or soybean cake as an organic nitrogen source for the fermentation of xanthan gum. See, for example, U.S. Pat. Nos. 3,020,206, 3,281,329 and 3,594,280 and "Materials and Methods in Fermentation", pp. 126–127 by G. L. Solomons, Academic Press, New York (1969). At a concentration in the fermentation broth of 0.4 weight %, Distillers Dried Solubles imparts a calcium content of 150.8 ppm to the fermentation broth while at a concentration of 0.45 weight % in the fermentation broth soybean meal imparts a calcium content of 16.7 ppm to the fermentation broth. The gum produced at a concentration of about 2.1–2.3% with the use of such organic nitrogen sources would have a calcium content of about 0.66–0.72% calcium in the case of Distillers Dried Solubles and about 0.07–0.08% in the case of soybean meal because xanthan gum binds all available calcium ion up to a maximum level of about 2.6%, assuming that no other calcium is present in the water or other media component.

Xanthan gum is an anionic polysaccharide due to the presence of about 20% glucuronic acid and 4% pyruvate in the molecule. It has been experimentally determined that about 0.026 g of calcium will react with all of the carboxyl groups in 1 g of xanthan gum. In other words this amount of calcium is the stoichiometric amount based on the carboxyl groups in the xanthan gum molecule. From this relationship it can be calculated that for each 1% of xanthan gum in the final fermentation broth, a calcium concentration in the broth of 260 ppm is the stoichiometric quantity sufficient to react with all of the carboxyl groups in the xanthan gum molecule. The gum recovered from such a broth will have a calcium content of about 26,000 ppm. The % of carboxyl groups that will react with diminishing amounts of calcium can likewise be calculated. The relationship of calcium content to % of carboxyl groups bound is shown in Table 2.

TABLE 2

$Ca^{++}$ Concentration v. % Carboxyl Bound

| Total Ca Content of Media (ppm) | Xanthan Gum Concentration (%) | Ca Content of Xan. Gum (ppm) | % Carboxyl Groups Bound |
|---|---|---|---|
| 260 | 1 | 26,000 | 100 |
| 22 | 1 | 2,200 | 8.5 |
| 7 | 1 | 700 | 2.7 |
| 4 | 1 | 400 | 1.6 |
| 2 | 1 | 200 | 0.8 |
| 520 | 2 | 26,000 | 100 |
| 44 | 2 | 2,200 | 8.5 |
| 14 | 2 | 700 | 2.7 |
| 8 | 2 | 400 | 1.6 |
| 4 | 2 | 200 | 0.8 |
| 650 | 2.5 | 26,000 | 100 |
| 55 | 2.5 | 2,200 | 8.5 |
| 17.5 | 2.5 | 700 | 2.7 |
| 10 | 2.5 | 400 | 1.6 |
| 5 | 2.5 | 200 | 0.8 |

Thus, the xanthan gum of the present invention can be described chemically as xanthan gum in which up to about 1.6% of the carboxyl groups are bound to calcium and the remaining carboxyl groups are bound to sodium, potassium, a mixture of sodium and potassium or other non-calcium cations.

The best evidence presently available suggests that xanthan gum has the formula:

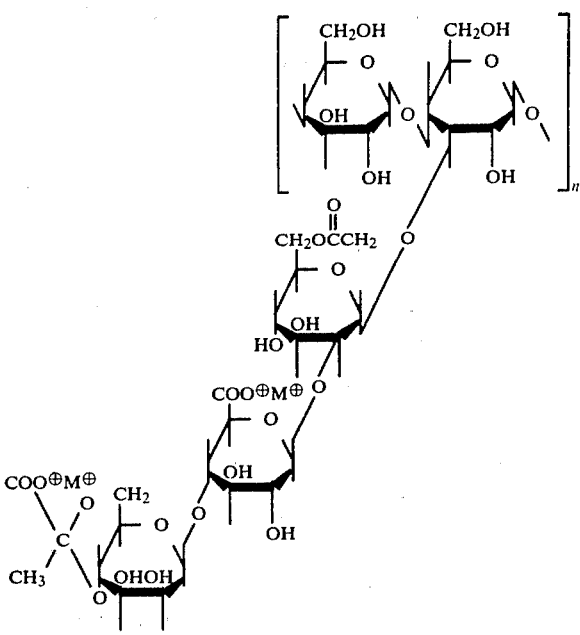

wherein $M^+$ is $Na^+$, $K^+$, or $\frac{1}{2} Ca^{++}$. Estimates of the molecular weight range from 2–50 million. The organism Xanthomonas produces this gum as an acid, the ratio of $Na^+ : K^+ : Ca^{++}$ in the recovered gum depending on the fermentation media conditions. It is now thought that under normal fermentation conditions calcium ions cause cross-linking between the side chains of different gum molecules. The greater the cross-linking the greater the viscosity of aqueous solutions and the higher the molecular weight. By producing xanthan gum under low calcium conditions, the amount of cross-linking is reduced. By producing xanthan gum under low calcium, high shear conditions, cross-linking is thought to be substantially prevented and the gum exhibits smooth flow properties. Where high shear is applied after fermentation is substantially complete, the effect of agitation is minimal since the calcium appears to be cheated by the xanthan gum molecule and the energy levels involved are not high enough to break the bonds. Thus, it is essential in one process that both low calcium and high shear co-exist while the organism Xanthomonas produces xanthan gum in its acid form in order to make the smooth flow gum of this invention.

In the novel process of this invention high shear is not necessary. Rather, 0.5% phosphate (0.45% $Na_2HPO_4$ and 0.05% $K_2HPO_4$) is added to the medium at the beginning of the final fermentation process and another 0.5% $Na_2HPO_4$ is added at the end of the process prior to precipitation. In a variation of this process 0.7% phosphate is added at the beginning of fermentation and none at the end. Thus, if between 0.7% and 1% phosphate is used in the final fermentation process, the necessity of high shear conditions is obviated.

As indicated above, production of the acid form of xanthan gum, the starting material in the practice of the present invention, by Xanthomonas campestris, NRRL B-1459, under a variety of fermentations conditions is well known. The inventive feature of this application relates to the maintenance of low calcium conditions in the fermentation broth (with or without high shear), which is independent of the biosynthetic pathway of the Xanthomonas organism in its production of the acid form of xanthan gum. It would be apparent therefore to one skilled in the art that the invention is operative using either B-1459 or a proprietary mutant strain of *Xanthomonas campestris* known by applicant's assignee to produce the acid form of xanthan gum in somewhat higher yields than does B-1459. Since the function of the microorganism is merely to produce said acid form of xanthan gum, availability of this mutant strain is not significant to the practice of this invention.

During the fermentation of xanthan gum, the fermentation broth is continually monitored to assure good mixing. As the viscosity of the broth increases with the amount of gum produced, frequent monitoring and a corresponding increase in agitation rate assures that all parts of the broth are properly aerated. The criterion of good mixing, well known to those skilled in the polysaccharide fermentation art, is sufficient to produce the low calcium xanthan gum of this invention.

When it is desired to produce the low calcium xanthan gum having smooth flow properties, high shear is required during the fermentation process unless 0.7% to 1% phosphate is used. The following agitation conditions have been found to be adequate to produce the low calcium, smooth flow xanthan gum of this invention. Agitation comparable to these agitation conditions is defined herein as "high shear".

| Fermentor Size | Agitation Conditions |
|---|---|
| 5 Liter | Three 3-½" flat turbine impellors. The initial agitation is set at 400 RPM's (105 ft/min) and is typically increased to 800-1000 RPM's (211-263 ft/min) by 16-24 hours. |
| 14 Liter | Three 2-15/16" flat blade impellors. The fermentation is started with an agitation rate of 400 RPM's (98 ft/min) and is typically increased to 1000 RPM's (245 ft/min) by 16-24 hours. The agitation can be increased as necessary to provide high shear up to 1500 RPM's (368 ft/min). |
| 30 Liter (8 Gallon) | Two 5-1/16" V-shaped turbine impellors. The initial agitation is 300 RPM's (127 ft/min) which is increased to 700 RPM's (295 ft/min) by 16-24 hours. |
| 70 Liter | Two 5-15/16" flat blade turbine impellors and one 6" propellor. This fermentor is started with an agitation rate of 300 RPM's (149 ft/min) and increased to 600 RPM's (297 ft/min) by 16-24 hours. It can be increased thereafter as needed to provide high shear to a maximum of 750 RPM's (371 ft/min). |
| 1500 Gallon | 3 sets (five 2-½" × 4" blades/set) of disc and turbine impellors; 20" diam. disc., 28" diam. impellor; 150 RPM. |

The high shear must be imparted to the beer during the fermentation process. If the beer is subjected to high shear after the fermentation is completed, the resulting gum does not exhibit smooth flow. Likewise, it is preferred to continue the high shear conditions throughout the entire fermentation process.

The smooth flow obtainable with the low calcium xanthan gum of the present invention is liable, in some cases, to be degraded by high temperature pasteurization conditions. For this reason, it is preferable to pasturerize at temperatures which do not exceed about 80° C.

A correlation has been found between the smooth flow property of the xanthan gum of this invention and the viscosity of an oil/water emulsion made up from the gum. The following test protocol can therefore be followed to determine whether a low calcium xanthan gum can also be characterized as having smooth flow.

TEST METHOD 1

3.5 g of low calcium xanthan gum is slurried in 20 g of vegetable oil. The slurry is added to 300 ml tap water in a Sunbeam solid state Waring blender and mixed for 20 seconds at the lowest speed (stir button). Mixing is stopped, 13 g of NaCl is added, and the mix is agitated at the highest speed (liquify button) for 10 seconds. The entire emulsion is poured into a 400 ml beaker and viscosity readings are obtained at room temperature on a Brookfield LVF viscometer, spindle 3 at 60 rpm. The xanthan gum used should contain between 86 and 92% solids and should be milled so that at least 98% passes through an 80 mesh screen and less than 40% passes through a 325 mesh screen. A low calcium xanthan gum is smooth flow if under these conditions viscosity readings of less than 1650 cP are obtained. It is preferred that the viscosity be less than 1600 cP.

Alternative, although less reliable, tests require visual observations. For example, the emulsion prepared as above is observed while being poured and its flow characteristics noted. A beaker containing such an emulsion is swirled so that its sides are coated and then the sides are observed. If the coating of emulsion on the sides is generally homogeneous rather than streaked and uneven, the gum can be considered to be smooth flow.

The low calcium xanthan gum of this invention can be used for any of the uses to which xanthan gum can be put. In addition, when still in the fermentation broth it is the intermediary for producing the smooth-flow low calcium xanthan gum of this invention.

Smooth-flow xanthan gum finds applicability in a variety of areas. First, to the extent that its properties are similar to those of xanthan gum, it can be used as a substitute in formulations requiring xanthan gum. However, the smooth flow xanthan gum of this invention is particularly useful in pourable and spoonable salad dressings. Solubility is markedly improved in reconstituted dry mixes such as fruit flavored beverages, cocoa drinks, gravies, and soups. Texture and flow properties are markedly improved in high sugar/solids systems such as sugar syrups, toothpaste, shampoo, hand cream, and fruit preserves. Representative usage levels are:

| | % by Weight |
|---|---|
| No/low oil salad dressing | 0.5-1.5 |
| High oil salad dressing | 0.2-0.8 |
| Toothpaste | 0.7-2.0 |
| preferably | 1.0-1.2 |
| Dry Foodstuffs (dispersible) | 0.2-1.5 |

Representative formulations using smooth flow xanthan gum of this invention are as follows:

Salad Dressing

To 40 parts of sugar add 20 parts of instant starch and 5 parts of smooth flow xanthan gum. Dry blend and then disperse in 410 parts of water. Mix until dissolved and add 60 parts of sugar. Mix in 20 parts of salt, 5 parts of mustard and 40 parts of fresh egg yolks. Using a fast whip beater mix in 300 parts of corn oil and 100 parts of 100 grain vinegar.

Orange Flavored Drink Mix

A drink is prepared by adding the following blended ingredients to 1 quart (944 ml) cold water and stirring for 30 seconds.

|  | Gms. |
|---|---|
| Baker's Special Sugar | 125.713 |
| Citric Acid, granulated anhydrous | 4.55 |
| Sodium Citrate, fine granular hydrous | 1.05 |
| Artificial Orange Juice Flavor 24825 (American Flavor and Fragrance Corp.) | 0.504 |
| Ascorbic Acid | 0.49 |
| Orange Essence Oil 1939 (Borden) | 0.336 |
| Smooth Flow Xanthan Gum | 0.28 |
| Kowet Titanium Dioxide (Kohnstamm) | 0.042 |
| FD&C Yellow No. 5 | 0.021 |
| FD&C Yellow No. 6 | 0.014 |
|  | 133.0 |

Toothpaste

Using known processes, a toothpaste is prepared from the following ingredients:

|  | % by Weight |
|---|---|
| Dicalcium phosphate dihydrate | 45.0 |
| Glycerine | 12.5 |
| Sorbitol | 12.5 |
| Sodium lauryl sulfate | 1.5 |
| Saccharin | 0.2 |
| Flavoring agent | 1.0 |
| Water | 26.3 |
| Smooth Flow Xanthan Gum | 1.0 |

The resulting paste has short, non-stringy flow, whereas a paste made with regular xanthan gum has noticeable stringiness.

Instant Hot Cream Soup Mix

An instant soup is prepared by adding the following blended ingredients to ¾ cup (180 ml) boiling water and stirring for 2 minutes.

|  | Gms. |
|---|---|
| Star Dri 24F Corn Syrup Solids (Staley) | 6.56 |
| Veg Cream (types) (Nestle) | 3.75 |
| Gelatinized Dura Jel (Staley) | 3.00 |
| Milk Solids Non-fat (instantized) | 2.50 |
| Salt | 1.50 |
| Sugar | 1.00 |
| MSG | 0.90 |
| Powdered onion | 0.20 |
| Maggi Hydrolyzed Plant Protein (Nestle) | 0.10 |
| Smooth flow xanthan gum | 0.25 |

Low calcium xanthan gum at a level of 0.1 to 2% by weight is also useful as a thickener for water-glycol fire resistant hydraulic fluids. These fluids comprise water, a low molecular weight glycol, a thickener, and various additives used for corrosion inhibition, anti-wear, etc. Low calcium xanthan gum is soluble in the various water-glycol mixtures which are used as vehicles for the fluids. Glycols such as ethylene glycol, diethylene glycol, and propylene glycol are used, at levels up to the weight of water present, to impart freezing point depression and low temperature fluidity to the fluids. Water-glycol mixtures have very poor lubricant and anti-wear properties; the thickener is used in water-glycol hydraulic fluids to provide these functions.

The following examples further illustrate the present invention without, however limiting the same thereto.

EXAMPLE 1

The media and media ingredients are prepared in deionized water to minimize the presence of calcium.

The flask seed medium is YM broth (Difco). These flasks are inoculated with a loopful of a strain of *Xanthomonas campestris* NRRL B-1459 grown on nutrient agar (Difco) or YM agar plates. The inoculated flasks are placed on a gyrotary shaker (New Brunswick Scientific, Inc.) at a shaking speed of 200-300 rpm. The temperature is controlled at 28°-33° C.

After 18-40 hours these seeds are used to inoculate a five-liter fermentor vessel containing three liters of a medium containing the following ingredients:

| 3.0% | Dextrose |
|---|---|
| 0.05% | Promosoy 100 (Central Soya) |
| 0.09% | $NH_4NO_3$ |
| 0.5% | $Na_2HPO_4$ |
| 0.01% | $MgSO_4 . 7H_2O$ |

The medium also contains trace elements such as $BO_3^{---}$, $Mn^{++}$, $Fe^{++}$, $Cu^{++}$, $Zn^{++}$, $Co^{++}$, $MoO_4^{--}$, and an antifoam agent (Sag 471).

The fermentation temperature is controlled at 28°-33° C. with the agitation rate set so that proper mixing of the fermentor contents occurs. Sterile air is supplied at a rate of 0.2-1.0 (v/v). After 18-40 hours, this seed is used to inoculate either 50 L of similar medium in a 70 L fermentor, or 20 L of such medium in a 30 L fermentor. This medium is composed of the following ingredients:

| 3.0% | Dextrose |
|---|---|
| 0.5% | $Na_2HPO_4$ |
| 0.09% | $NH_4NO_3$ |
| 0.01% | $MgSO_4 . 7H_2O$ |
| 0.05% | Promosoy 100 |

In these fermentors, the pH is controlled in the range of 6.0-7.5 using KOH addition. Aeration is similar to that in the smaller fermentor. The agitation is increased as necessary to maintain high shear. The agitation in the 30 L fermentors is supplied by two 5-1/16" V-shaped turbine impellors. The initial agitation is 300 RPM's (127 ft/min) which is increased to 700 RPM's (295 ft/min) by 16-24 hours. The agitation in the 70 L fermentor is supplied by two 5-15/16" flat blade turbine impellors and one 6" propellor. This fermentor is started with an agitation rate of 300 RPM's (149 ft/min) and increased to 600 RPM's (297 ft/min) by 16-24 hours. It can be increased thereafter as needed to a maximum of 750 RPM's (371 ft/min). The fermentation is terminated when the carbon source has been fully utilized.

The fermentation broth is pasteurized in the fermentation vessel at 75° C. for 15 minutes. The product is recovered by alcohol precipitation. The recovered fibers are dried for 2 hours in a steam oven at 55° C. followed by milling through a 20-mesh screen. This product, designated sample 1, is a low calcium, smooth flow xanthan gum.

A second batch is prepared following the procedure of sample 1 but using Distillers Solubles as the organic nitrogen source and tap water instead of deionized water. This product, sample 2, is representative of commercially available xanthan gum.

A third batch is prepared using the same conditions as those used to prepare sample 1 except that deionized water containing 40 ppm added calcium is used in the media. This product, designated sample 3, is also comparable to commercially available xanthan gum.

EXAMPLE 2

1. Seed Preparation

Fresh YM agar plate cultures of *X. campestris* B-1459 are used to inoculate YM broth flasks. The inoculated flasks are placed on a gyrotary shaker at a shaking speed of 200-300 rpm. At 24-30 hrs., these flasks are used to inoculate flasks containing the following components:

| Component | Amount |
|---|---|
| Starch | 2.67% |
| $Na_2HPO_4$ | 0.50% |
| Promosoy 100 | 0.19% |
| $NH_4NO_3$ | 0.09% |
| NZ Amine A | 0.03% |
| $MgSO_4 \cdot 7H_2O$ | 0.02% |
| $FeSO_4 \cdot 7H_2O$ | 5 ppm |
| HoLe salts | 1 ml/L |
| Balab | 0.26% |
| Defoamer (Sag) | 0.02% |
| *Tap Water | ≈96.22 |

*The starch slurry is prepared in tap water for hydrolysis and represents 10% of the final fermentor volume.

The fermentation temperature is controlled at 28°-33° C. with the agitation rate set so that proper mixing of the fermentor contents occurs. Sterile air is supplied at a rate of 0.2-1.0 (v/v). The flasks are used at 24-35 hrs. to inoculate 14-liter fermentors with a 6-7% inoculum level.

2. Final Fermentor

Fermentors of a 14-liter capacity are used for the final fermentation containing about 10 liters of the following medium:

| Component | Amount |
|---|---|
| Corn syrup | 4.2% |
| $Na_2HPO_4$ | 0.053% |
| Promosoy 100 | 0.0336% |
| $MgSO_4 \cdot 7H_2O$ | 0.02% |
| $NH_4NO_3$ | 0.106% |
| $FeSO_4 \cdot 7H_2O$ | 5 ppm |
| HoLe salts | 1 ml/L |
| Defoamer (Sag) | 0.01% |
| Deionized water | ≈95.58% |

The $FeSO_4 \cdot 7H_2O$ and HoLe salts are autoclaved separately. Alternatively, they are filtered instead of being added directly to the medium to be autoclaved.

The pH is controlled with 25% NaOH or KOH at 6.0-7.5. Aeration is similar to that in the smaller fermentor.

Agitation is supplied by three 2-15/16" flat blade impellors. The fermentation is started at an agitation rate of 400 rpm's (98 ft/min) and is increased to 1000 rpm's (245 ft/min) by 16-24 hours. The agitation can be increased as necessary to provide high shear up to 1500 rpm's (368 ft/min).

Fermentation is terminated when the carbon source is less than 0.1%.

The fermentation broth is pasteurized in the fermentation vessel at 75° C. for 15 minutes. The product is recovered by alcohol precipitation. The recovered fibers are dried for 2 hours in a steam oven at 55° C. followed by milling through a 20-mesh screen. The product is a low calcium, smooth-flow xanthan gum.

EXAMPLE 3

Low Calcium, Smooth Flow Xanthan Gum Seed Preparation

The flask seed medium is YM (Difco) broth. Flask size is 500 ml Erlenmeyer containing 100 ml of broth. The flasks are inoculated with a loopful of cells of a culture of *X. campestris* maintained on nutrient agar plates and incubated at 30° C. on gyrotary shakers at 300-400 rpm for 24-48 hrs. At this point two such flasks are used to seed a 5 L New Brunswick scientific fermentor containing 3 L (final volume) of the following medium:

| Amount | Component |
|---|---|
| D. I. | Water |
| 2.67% | Starch (prepared in tap water, 300 ml, and liquified with Tenase [Miles], a commercially available α-amylase) (Autoclaved separately) |
| 0.01 | $MgSO_4 \cdot 7H_2O$ |
| 0.5% | $Na_2HPO_4$ |
| 0.19% | Promosoy 100 |
| 0.09% | $NH_4NO_3$ (Autoclaved separately) |
| 0.03% | NZ Amine |
| 1 | ppm $Fe^{++}$ (filter sterilized) |
| 1 | ml/L HoLe salts (filter sterilized) |
| 2 | ml SAG 471 Defoamer |

These seeds are used at 24-48 hrs. to seed a 20 L fermentor. The medium used in this fermentor is as follows:

| Amount | Component |
|---|---|
| D. I. | Water |
| 3.9% | 42 DE Corn Syrup (autoclaved separately) |
| 0.01% | $MgSO_4 \cdot 7H_2O$ |
| 0.09% | $NH_4NO_3$ (autoclaved separately) |
| 0.10% | $Na_2HPO_4$ |
| 0.0336% | Promosoy 100 |
| 1 | ml/L HoLe salts (filter sterilized) |
| 1 | ppm $Fe^{++}$ (filter sterilized) |
| 5 | ml SAG 471 Defoamer |

The fermentation is run at 30° C. until residual carbon source level is less than 0.2%. Starting agitation in 300 RPM and aeration is 10 L/M. Air remains constant throughout fermentation. Agitation increases as fermentation broth increases in viscosity. The pH is controlled at pH 6.8 by the addition of 25% KOH as necessary with automatic pH controllers.

The fermentation liquor is pasteurized at 75° C. for 15 minutes, cooled and precipitated in approximately 2-3 volumes of 99% isopropanol. The fibers are collected and dried in a forced air tray drier at 50°-55° C. for approximately two hours and then milled to a powder, identified as BD-93.

The product is the low calcium, smooth flow xanthan gum of this invention.

EXAMPLE 4

Xanthan Gum

Following the procedure of Example 3 but using tap water containing approximately 80 ppm $Ca^{++}$ instead of D.I. water and adding 0.008% $Ca^{++}$ to the final fermentation medium (thus having a total of 160 ppm $Ca^{++}$ in said medium), there is produced a product representative of commercially available xanthan gum. This product is identified as BD-94.

EXAMPLE 5

Comparison of Low Calcium vs. Regular Xanthan Gums

BD-93, BD-94, and commercially available xanthan gum are compared to determine the effect of low calcium fermentation conditions on their rheological properties.

The viscosities of the gum samples (1% and 2% w/w, in deionized (D.I.) water and 1% w/w KCl solution) and low oil emulsions are determined using a Brookfield LVF viscometer, at 60 rpm and appropriate spindle.

A slurry of each gum (6.4 g) in Kraft vegetable oil-specially processed soybean oil (40 g) is added to 500 ml of water with stirring. After hydration, sodium chloride (26 g) and 10% acetic acid (75 ml) are added. The emulsions are milled in a Sterling colloid mill at a setting of 0.015".

Working yield values are determined from the viscosity profiles at low shear rates obtained by using the spring relaxation method on the Wells-Brookfield RVT plate and cone viscometer. (See Jeanes et al., (1973) J. Appl. Polymer Sci. 17 pp. 1621–1624. The working yield value is defined as the shear stress (dynes/cm$^2$) required to produce a shear rate of 0.01 sec$^{-1}$.

Visual observation of flow properties are determined by pouring low oil emulsions from container to container. Flow properties are rated as "smooth" through "light chunky", "medium chunky" to "heavy chunky".

A quantitative determination of flow properties is carried out by measurement of the flow rate of gum solutions (1% w/w in 1% KCl) and emulsions in a Bostwick Consistometer. This instrument which is available from Central Scientific Co., Inc., 26005 Kostner Avenue, Chicago, Ill. 60623 determines consistency by measuring the distance that a material flows under its own weight during a given time interval. The distance travelled by the moving front after 5 minutes is a reproducible measure of the flow properties (degree of smoothness) of the solutions.

|  | BD-93 | Commercial Xanthan Gum | BD-94 |
|---|---|---|---|
| Calcium Content (ppm) | 130 | 2322 | 4357 |
| Magnesium Content (ppm) | 391 | 914 | 1019 |
| 1% Viscosity, D.I. H$_2$O (cP, 60 rpm, spindle 3) | 410 | 810 | 815 |
| 1% Viscosity, 1% KCl (cP, 60 rpm, spindle 3) | 1075 | 1250–1550 | 1175 |
| Working Yield Value, 1% Gum, D.I. H$_2$O (dynes/cm$^2$) | (1) | 15.5 | 26 |
| Working Yield Value, 1% Gum, 1% KCl (dynes/cm$^2$) | 22 | 52 | 42 |
| 2% Viscosity, D.I. H$_2$O (cP, 60 rpm) | 1040 | N.D. | 1710 |
| 2% Viscosity, 1% KCl (cP, 60 rpm, spin. 4) | 4070 | N.D. | 4080 |
| 2% D.I. Solution Visual Flow Characteristic | Smooth | Chunky | Chunky |
| Working Yield Value, 2% Gum, D.I. H$_2$O (dynes/cm$^2$) | 16 | N.D. | 52 |
| Visual Flow Characteristic of Low Oil Emulsion | Smooth | Medium to Heavy Chunky | Light to Medium Chunky |
| Low Oil Emulsion Viscosity (60 rpm) | 1390 | 1410 | 1490 |
| Low Oil Emulsion Working Yield Value (dynes/cm$^2$) | 45 | N.D. | 82 |
| Bostwick Test, Distance Covered After 5 min (cm) |  |  |  |
| 1% Gum and 1% KCl | 17.2 | 10.9 | 12.7 |
| Low Oil Emulsion | 13.2 | N.D. | 9.7 |

(1) Too low to determine due to low viscosity (<800 cP) in D.I. water
N.D. = Not Determined

EXAMPLE 6

Effect of Pasteurization Temperature on Smooth Flow Property

*X. campestris* is fermented under low calcium high shear conditions substantially similar to those described in Example 3 except that a 70 liter final fermentor is used. Following fermentation, samples of the fermentation broth are removed from the fermentor and pasteurized at various temperatures and times using the copper coil immersed in a hot oil bath. The fermentation broth remaining in the fermentor is pasteurized in place at 75° C. for various times. Using these procedures, samples BD-118 through BD-125 are prepared.

The xanthan gum in these samples is precipitated with 2–3 volumes of 99% isopropyl alcohol. The fibrous product is dried overnight in a 45° C. oven followed by milling through a 20-mesh screen.

Upon analysis the following data are obtained.

| Sample No. | Calcium Content (ppm) | Pasteurization Conditions | Emulsion Viscosity (cP) | Emulsion Flow Properties Visual | Bostwick |
|---|---|---|---|---|---|
| BD-118 | 145 | No pasteurization | 1165 | Smooth | 14.0 |
| BD-122 | 145 | 75° C. 2-3 min., coil | 1215 | Smooth | 13.8 |
| BD-123 | 140 | 75°-78° C. 8-10 min., coil | 1340 | Smooth | 12.1 |
| BD-124 | 140 | 79° C. 2-3 min., coil | 1240 | Smooth | 12.5 |
| BD-125 | N.D. | 99° C. 2-3 min, coil | 1215 | Smooth | 12.8 |
| BD-119 | 135 | 75° C. 2-3 min., steam | 1310 | Smooth | 12.7 |
| BD-120 | N.D. | 75° C. 5 min, steam | 1180 | Smooth | 13.3 |
| BD-121 | 140 | 75° C. 15 min., steam | 1270 | Smooth | 13.6 |

N.D. Not determined

Note:
These samples were prepared from the same batch of broth, and therefore should have identical Ca contents. This is confirmed by analysis for calcium, which results are indicated above, wherein differences are within experimental error.

EXAMPLE 7

Effect of Pasteurization Temperature On Smooth Flow Property

*X. campestris* is fermented under substantially the same procedure as in Example 6. Following fermentation, samples of the fermentation broth are removed from the fermentor and pasteurized at various times and temperatures by passing the broth through a copper coil immersed in hot oil bath, followed by rapid cooling using an ice bath. Samples BD-107 through BD-113 are prepared in this manner. BD-115 is an unpastuerized control.

| | |
|---|---|
| BD-107 | 79° C. for 2-3 minutes |
| BD-108 | 85° C. for 2-3 minutes |
| BD-109 | 91° C. for 2-3 minutes |
| BD-110 | 99° C. for 2-3 minutes |
| BD-111 | 79° C. for 10 minutes |
| BD-112 | 116° C. for 2-3 minutes |
| BD-113 | 99° C. for 5 minutes |
| BD-115 | No pasteurization (control) |

The xanthan gum in these samples is precipitated with alcohol, dried for two hours in a steam oven at 50°-55° C., and milled through a 20-mesh screen.

| Sample No. | Emulsion Viscosity (cP) | Emulsion Flow Properties Visual | Bostwick |
|---|---|---|---|
| BD-107 | 1610 | Light-medium | 10.5 |
| BD-108 | 1615 | Light-medium | 10.8 |
| BD-109 | 1535 | Light-medium | 10.5 |
| BD-110 | 1735 | Light-medium | 9.85 |
| BD-111 | 1540 | Light | 10.75 |
| BD-112 | 1635 | Light-medium | 10.3 |
| BD-113 | 1600 | Medium | 10.6 |
| BD-115 | 1360 | Smooth | 13.6 |

These samples are prepared from the same broth and therefore have identical Ca content.

EXAMPLE 8

Calcium Content of Gum vs. Flow Properties

Nine Samples of xanthan gum prepared under various different seed flask and final fermentor conditions are analyzed to compare their calcium content to their flow properties. The following data are obtained:

| Run | Ca (ppm) | Flow Properties (low oil/H$_2$O Emulsion) |
|---|---|---|
| 103-77C | 37 | Smooth |
| 102-77C | 123 | Slightly Chunky |
| 52-77B | 126 | Smooth |
| 100-77C | 193 | Slightly Chunky |
| 99-77C | 207 | Smooth |
| 97-77C | 315 | Slightly Chunky |
| 2-78C | 315 | Slightly Chunky |
| 90-77C | 478 | Chunky |
| 83-77C | 536 | Chunky |

EXAMPLE 9

Magnesium Content of Gum vs. Flow Properties

In order to demonstrate that the smooth flow property is dependent upon the calcium ion content of the fermentation broth in which the xanthan gum is produced, and is independent of magnesium ion content, the following comparisons are made with emulsions made using xanthan gums prepared from broths which result in final products having the indicated level of Ca$^{++}$ and Mg$^{++}$ (in ppm):

| Sample | Ca$^{++}$ | Mg$^{++}$ | Ca/Mg Ratio | Flow Properties of Low Oil Emulsion |
|---|---|---|---|---|
| 9-1 | 4357 | 1019 | 4.28 | Medium-Heavy Chunky |
| 9-2 | 2322 | 914 | 2.54 | Medium-Heavy Chunky |
| 9-3 | 1866 | 917 | 2.03 | Medium-Heavy Chunky |
| 9-4 | 772 | 388 | 1.99 | Light Chunky |
| 9-5 | 567 | 546 | 1.04 | Medium Chunky |
| 9-6 | 261 | 594 | 0.44 | Smooth |
| 9-7 | 153 | 546 | 0.28 | Smooth |
| 9-8 | 130 | 391 | 0.33 | Smooth |

Samples which have smooth flow properties are characterized by Ca$^{++}$ levels of 261 ppm or below.

EXAMPLE 10

An oil-well drilling fluid is made up in conventional manner from the following constituents: low calcium, smooth flow xanthan gum, (BD-93) 0.34 kg; water, 189.27 liters; bentonite, 3.63 kg; carboxymethyl cellulose 0.23 kg; and KCl, 4.76 kg. This mud exhibits the following properties:

| Fann Viscometer Dial Readings | Initial | Rolled 16 hrs. at 150° F. |
|---|---|---|
| 600 rpm | 31.3 | 27.7 |
| 300 rpm | 22.7 | 20.7 |
| 200 rpm | 19.3 | 17.4 |
| 100 rpm | 14.5 | 13.2 |
| 6 rpm | 6.1 | 5.3 |
| 3 rpm | 5.2 | 4.7 |
| Plastic Viscosity, cP | 8.6 | 7.0 |
| Yield Point, lb/100 ft$^2$ | 14.1 | 13.7 |
| API Filtrate, ml | 11.4 | 12.0 |

These results show the excellent characteristics of an oil-well drilling fluid of the invention. In particular, the high viscosity at low shear rates provides good hole cleaning and the low viscosity at high shear rates increases the penetration rate of the bit.

EXAMPLE 11

French Dressing

A French dressing is made using the following formulation:

| Ingredients | % | |
|---|---|---|
| Vegetable Oil | 38.00 | 38.00 |
| Water | 34.65 | 34.65 |
| Sugar | 11.50 | 11.50 |
| Vinegar (100 grain) | 9.00 | 9.00 |
| Salt | 4.00 | 4.00 |
| Paprika, powdered | 1.35 | 1.35 |
| Mustard, powdered | 1.25 | 1.25 |
| Low calcium, smooth flow xanthan gum | 0.25 | |
| Xanthan gum (Control) | | 0.25 |
| | 100.00% | 100.00% |

Procedure:
1. Dry blend xanthan gum with one-half of the sugar and hydrate with water and vinegar under vigorous agitation for 15 minutes.
2. Add blend of all remaining solids.
3. Add oil, slowly at first, then at normal rate.
4. Emulsify with a colloid mill at 0.02".

The flow properties of the dressings are measured in the Bostwick Consistometer using the procedure described in Example 5 with the following results:

BOSTWICK RESULTS

| | Distance in cm at Time Indicated | | | | | | | Visual Examination of |
|---|---|---|---|---|---|---|---|---|
| Seconds | 5 | 10 | 20 | 30 | 60 | 120 | 180 | Flow Properties |
| Xanthan Gum | | | | | | | | |
| Low calcium | 10.0 | 10.8 | 11.7 | 12.5 | 13.6 | 14.7 | 5.3 | Smooth |
| Control | 5.0 | 5.8 | 6.6 | 7.2 | 8.1 | 9.0 | 9.5 | Chunky |

EXAMPLE 12

Low Calorie French Dressing

A low calorie French dressing containing approximately 19 calories per fluid ounce or 3 calories per teaspoon is made using the following formulation:

| Ingredients: | % | |
|---|---|---|
| Water | 55.95 | 55.95 |
| Vinegar (50 grain) | 18.00 | 18.00 |

-continued

| Ingredients: | % | |
|---|---|---|
| Tomato Paste (26%) | 7.50 | 7.50 |
| Vegetable Oil | 6.00 | 6.00 |
| Lemon Juice | 5.00 | 5.00 |
| Salt | 3.50 | 3.50 |
| Egg Yolk (fresh) | 2.00 | 2.00 |
| Paprika | 0.60 | 0.60 |
| Mustard | 0.50 | 0.50 |
| Low calcium, smooth flow xanthan gum | 0.75 | |
| Xanthan gum (Control) | | 0.75 |
| Onion powder | 0.10 | 0.10 |
| Garlic powder | 0.05 | 0.05 |
| Non-nutritive sweetener | 0.05 | 0.05 |
| | 100.00% | 100.00% |

Procedure:
1. Disperse the xanthan gum in the water and add with good agitation to all oil, vinegar and lemon juice in which the mustard is dispersed. Complete hydration in 10–15 minutes with stirring.
2. After hydration, add tomato paste and egg yolk.
3. Add blend of all solids with stirring.
4. Emulsify with a colloid mill at 0.015" (0.038 cm).

The flow properties of the dressings are measured in the Bostwick Consistometer using the procedure described in Example 5 with the following results:

| | Distance in cm | | | | | | | Visual Examination of |
|---|---|---|---|---|---|---|---|---|
| Seconds | 5 | 10 | 20 | 30 | 60 | 120 | 180 | Flow Properties |
| Xanthan Gum | | | | | | | | |
| Low calcium | 7.5 | 8.0 | 8.5 | 8.7 | 9.3 | 9.8 | 10.2 | Smooth |
| Control | 4.0 | 4.7 | 5.4 | 5.7 | 6.2 | 6.6 | 6.8 | Chunky |

EXAMPLE 13

Test Method 1

Low calcium xanthan gum samples (FP-87, FP-81, FP-92, FP-103, and FP-478) are produced and compared to commercially available xanthan gum. These samples are tested according to Test Method 1 and by visual observation with the following results:

| Sample | Visc. (cP) | Flow (visual determination) |
|---|---|---|
| Xan. gum 1 | 2350 | Very Chunky |
| Xan. gum 2 | | |
| a[1] | 1670 | Chunky |
| b | 1830 | Chunky |
| c | 1800 | Chunky |
| Xan. gum 3 | | |
| a | 1800 | Chunky |
| b | 1730 | Chunky |
| c | 1800 | Chunky |

-continued

| Sample | Visc. (cP) | Flow (visual determination) |
|---|---|---|
| FP-87 | | |
| a | 1510 | Slightly Chunky |
| b | 1510 | Smooth |
| FP-81 | | |
| a | 1580 | Slightly Chunky |
| b | 1520 | Smooth |
| FP-92 | | |
| a | 1710 | Slightly Chunky |
| b | 1730 | Slightly Chunky |
| FP-103 | | |
| a | 1510 | Smooth |
| b | 1500 | Smooth |
| c | 1540 | Smooth |
| FP-478 | | |
| a | 1360 | Smooth |
| b | 1350 | Smooth |

[1] Letters indicate replicates of same sample, so that viscosity differences are within experimental error.

EXAMPLE 14

Pilot Plant Fermentation

Smooth-flow, low calcium xanthan gum is prepared in a 1500 gal. fermentor using soft water.

| | | |
|---|---|---|
| Inoculum: | Age - 54¼ hrs. | |
| (100 gals) | pH - 6.82 | |
| | Viscosity - 2550 cP | |
| Medium: | Corn Syrup (42 D.E.) | 3.96% |
| (1100 gals) | $NH_4NO_3$ | 0.106% |
| | $K_2HPO_4$ | 0.053% |
| | Promosoy 100 | 0.033% |
| | $MgSO_4 \cdot 7H_2O$ | 0.01% |
| | Balab Defoamer | 0.25% (v/v) |
| | K-60 Defoamer | 0.022 (v/v) |
| | KOH | To control pH at 6.0-7.5 |
| Fermentation: | | |
| | Beer pH | 7.06 |
| | Temperature | 30–31° C. |
| | Aeration | 0.2–1.0 (v/v) |
| Agitation: | Disc and turbine impellors | |
| | Number of sets: 3 | |
| | Number of blades/set: 5 | |
| | Disc diameter: 20 inches | |
| | Blade dimension: 2⅜" × 4" | |
| | Impellor diameter: 28" | |
| | Speed - 150 rpm | |
| Recovery: | Beer pH adjust to 6.0 with $H_2SO_4$ | |
| | Beer rate - 5 gpm | |
| | Pasteurization - 74° C./6 min | |
| | Ppt. with 3 volumes isopropanol | |

Following the procedure of Example 14 but replacing $K_2HPO_4$ with $Na_2HPO_4$, the smooth-flow, low calcium xanthan gum of the present invention is also produced.

EXAMPLE 15

Effect of Phosphate on Smooth Flow Property

Three batches of low calcium xanthan gum are prepared in 2000 gal. fermentors (1200 gal. working volume) to determine the effect of phosphate on the smooth flow property of low calcium xanthan gum. The fermentation media are essentially the same as in Example 14 except that 4.2% corn syrup and only 0.01% defoamer are used.

The baffles used are 5.5" W×144" L and are 1" from the inside of the fermentor wall.

The 28" diam. turbines each contain five 2.5" W blades.

The fermentor is 54" in width.

The fermentations last from 59–69 hours. The following data are obtained.

| | F-5-9-15 | F-5-1-17 | F-5-3-9 |
|---|---|---|---|
| Medium | As above | As above | As above but with 0.63% $Na_2HPO_4$ and 0.07% $K_2HPO_4$ |
| Baffles | 4 | 1 | 1 |
| Turbines | 3 | 1 | 1 |
| Emulsion Flow Characteristics | Smooth | Heavy Chunky | Smooth |

Thus, under high shear conditions, the smooth flow product of this invention is produced, whereas, under conditions which can be described as "good mixing" (i.e., sufficient to produce xanthan gum), the smooth flow product is not produced unless the phosphate level of the medium is significantly increased.

In an alternate process, 0.5% phosphate is added at the beginning of fermentation and another 0.5% is added after fermentation and prior to recovery.

Both these processes are particularly useful in production size fermentors to obviate the need for high shear.

What is claimed is:

1. In a process for preparing low calcium, smooth flow xanthan gum by the whole culture fermentation of *Xanthomonas campestris* in an aqueous medium containing up to about 4 ppm of calcium ion per each 1% of xanthan gum concentration in the completed fermentation broth the improvement which comprises adding from 0.7% to 1.0% phosphate to the medium.

2. The process of claim 1 which comprises adding 0.7% phosphate to the medium at the beginning of the final fermentation process.

3. The process of claim 2 where the phosphate is $Na_2HPO_4$.

4. The process of claim 1 which comprises adding 0.5% phosphate at the beginning of the final fermentation process and 0.5% phosphate at the end of the process prior to precipitation.

5. The process of claim 4 where the initial 0.05% phosphate comprises 0.45% $Na_2HPO_4$ and 0.05% $K_2HPO_4$.

* * * * *